(12) United States Patent
Koyakutty et al.

(10) Patent No.: US 10,806,805 B2
(45) Date of Patent: Oct. 20, 2020

(54) MRI AND CT CONTRAST-ENABLED COMPOSITE IMPLANTS FOR IMAGE-GUIDED TISSUE REGENERATION AND THERAPY

(71) Applicant: AMRITA VISHWA VIDYAPEETHAM, Kochi (IN)

(72) Inventors: Manzoor Koyakutty, Kochi (IN); Sajesh K. Meethaleveedu, Kochi (IN); Anusha Ashokan, Kochi (IN); Vijay Harish Somasundaram, Kochi (IN); Shantikumar Nair, Kochi (IN)

(73) Assignee: Amrita Vishwa Vidyapeetham, Kochi (IN)

( * ) Notice: Subject to any disclaimer, the term of this patent is extended or adjusted under 35 U.S.C. 154(b) by 0 days.

(21) Appl. No.: 16/081,931

(22) PCT Filed: Mar. 3, 2017

(86) PCT No.: PCT/US2017/020793
§ 371 (c)(1),
(2) Date: Sep. 3, 2018

(87) PCT Pub. No.: WO2017/152127
PCT Pub. Date: Sep. 8, 2017

(65) Prior Publication Data
US 2019/0054196 A1    Feb. 21, 2019

(30) Foreign Application Priority Data
Mar. 3, 2016   (IN) .............................. 201641007472

(51) Int. Cl.
| | | |
|---|---|---|
| A61L 27/56 | (2006.01) | |
| A61K 49/18 | (2006.01) | |
| A61K 9/00 | (2006.01) | |
| A61L 27/50 | (2006.01) | |
| A61K 49/00 | (2006.01) | |
| A61K 49/04 | (2006.01) | |
| A61L 27/46 | (2006.01) | |
| A61B 5/055 | (2006.01) | |
| A61K 49/14 | (2006.01) | |
| A61L 27/02 | (2006.01) | |
| A61L 27/20 | (2006.01) | |
| A61L 27/22 | (2006.01) | |
| A61L 27/44 | (2006.01) | |
| A61L 27/54 | (2006.01) | |
| A61K 47/42 | (2017.01) | |
| A61K 47/02 | (2006.01) | |
| G01R 33/58 | (2006.01) | |

(Continued)

(52) U.S. Cl.
CPC .......... *A61K 49/1818* (2013.01); *A61B 5/055* (2013.01); *A61K 9/0024* (2013.01); *A61K 49/0002* (2013.01); *A61K 49/04* (2013.01); *A61K 49/0419* (2013.01); *A61K 49/0457* (2013.01); *A61K 49/14* (2013.01); *A61K 49/1803* (2013.01); *A61L 27/025* (2013.01); *A61L 27/20* (2013.01); *A61L 27/222* (2013.01); *A61L 27/446* (2013.01); *A61L 27/46* (2013.01); *A61L 27/50* (2013.01); *A61L 27/54* (2013.01); *A61L 27/56* (2013.01); *A61B 6/481* (2013.01); *A61K 9/19* (2013.01); *A61K 47/02* (2013.01); *A61K 47/36* (2013.01); *A61K 47/42* (2013.01); *A61L 2300/414* (2013.01); *A61L 2400/12* (2013.01); *A61L 2430/00* (2013.01); *A61L 2430/02* (2013.01); *G01R 33/4812* (2013.01); *G01R 33/5601* (2013.01); *G01R 33/58* (2013.01)

(58) Field of Classification Search
CPC ............ A61K 49/0002; A61K 49/1818; A61K 9/0024; A61L 27/56
See application file for complete search history.

(56) References Cited

U.S. PATENT DOCUMENTS

| | | |
|---|---|---|
| 2010/0183515 A1 | 7/2010 | Hart et al. |
| 2011/0027189 A1 | 2/2011 | Markov et al. |
| 2013/0211249 A1 | 8/2013 | Barnett et al. |

FOREIGN PATENT DOCUMENTS

| | | | | |
|---|---|---|---|---|
| WO | 2010062678 A2 | 6/2010 | | |
| WO | WO-2010062678 A2 * | 6/2010 | ........... | A61K 9/0019 |

(Continued)

OTHER PUBLICATIONS

International Preliminary Report on Patentability Chapter I for Application No. PCT/US2017/020793, dated Sep. 4, 2018, 6 pages.

(Continued)

*Primary Examiner* — Micah Paul Young
(74) *Attorney, Agent, or Firm* — Convergence Intellectual Property Law P.C.; Jonathan Garfinkel

(57) ABSTRACT

A composite implant for providing simultaneous magnetic resonance imaging (MRI) and computed tomographic (CT) imaging contrast is disclosed. The composite implant is formed of a calcium compound in the form of nano or microparticles doped with a first dopant configured to provide MRI contrast and a second dopant configured to provide CT contrast. The calcium compound is loaded onto a polymer gel matrix and lyophilized to form a mass with 3-dimensionally interconnected porosity, configured to provide tissue integration and proliferation sites. Methods of forming the composite implant are also disclosed. The implant could be a scaffold or bead structured to enable treatment of human or animal patient for bone/cartilage injury or defect by implantation, with MRI and CT monitoring.

14 Claims, 12 Drawing Sheets

(51) Int. Cl.
    *A61K 47/36*     (2006.01)
    *A61K 9/19*     (2006.01)
    *A61B 6/00*     (2006.01)
    *G01R 33/48*     (2006.01)
    *G01R 33/56*     (2006.01)

(56) References Cited

FOREIGN PATENT DOCUMENTS

| WO | 2014141288 A1 | 9/2014 | |
|---|---|---|---|
| WO | WO-2014141288 A1 * | 9/2014 | ............ A61K 9/0009 |

OTHER PUBLICATIONS

International Search Report and Written Opinion for Application No. PCT/US2017/020793, dated May 23, 2017, 7 pages.

* cited by examiner

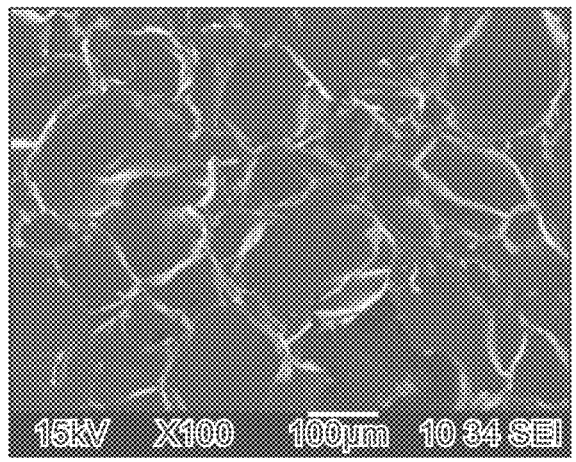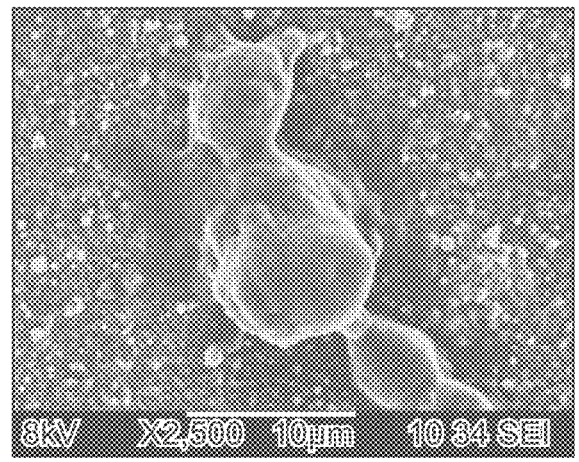
FIG. 3A FIG. 3B
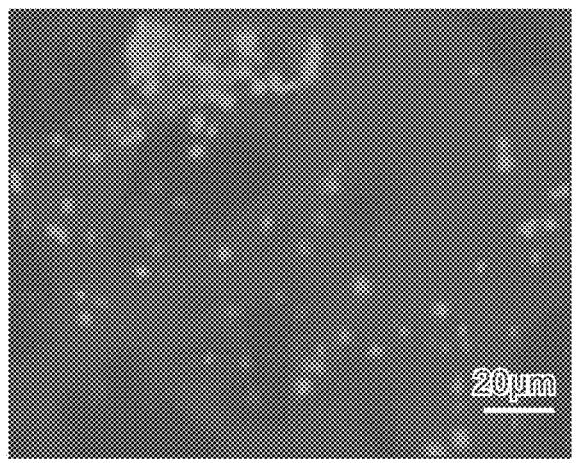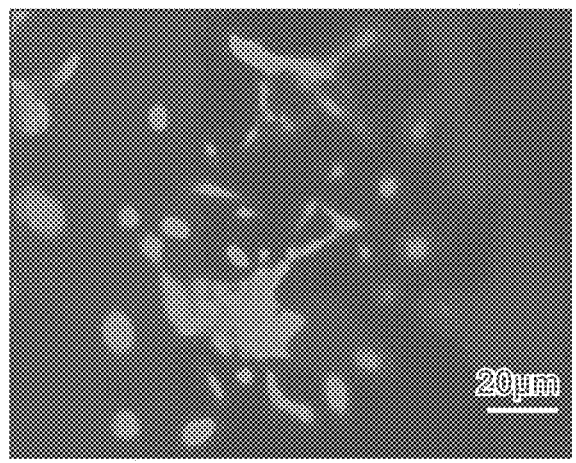
FIG. 3C FIG. 3D

MRI AND CT CONTRAST-ENABLED COMPOSITE IMPLANTS FOR IMAGE-GUIDED TISSUE REGENERATION AND THERAPY

CROSS-REFERENCES TO RELATED APPLICATIONS

This application is a National Stage of International application No. PCT/US2017/020793 entitled "MRI AND CT CONTRAST-ENABLED COMPOSITE IMPLANTS FOR IMAGE-GUIDED TISSUE REGENERATION AND THERAPY" filed on Mar. 3, 2017, which claims priority to Indian Provisional Patent Application No. 201641007472 entitled "MRI AND CT CONTRAST ENABLED 3D SCAFFOLDS AND BEADS FOR IMAGE GUIDED TISSUE REGENERATION", filed on Mar. 3, 2016, the full disclosure of which is incorporated herein by reference.

FIELD OF THE INVENTION

The invention generally relates to composite implants for tissue regeneration and in particular to osteoconductive 3-D scaffold and beads, method of preparation thereof and use thereof in magnetic resonance imaging (MRI) and/or computed tomography (CT) contrast enabled treatment.

BACKGROUND

Non-invasive monitoring of tissue regeneration is turning out to be of particular importance as it can provide information about various stages of tissue growth without compromising the biochemical and mechanical properties of the samples. Among the diverse non-invasive imaging techniques available, Magnetic Resonance Imaging (MRI) and Computed Tomography (CT) can be considered as useful tools to monitor tissue development, both in vitro and in vivo. With high resolution and excellent penetration depth, these imaging techniques can provide information with respect to various stages of bone regeneration, bone structure and density. However, insignificant difference in contrast change between host tissue and implanted biomaterial based scaffold often limits the application of MRI and CT for detecting tissue regeneration. Hence, in a clinical translational perspective, tissue engineered implants must exhibit sufficient sensitivity for non-invasive localization and functional assessment using MRI and CT.

SUMMARY OF THE INVENTION

The present invention relates to a composite implant that provides simultaneous magnetic resonance imaging (MRI) and computed tomographic (CT) imaging contrast, and a method for making the same.

A composite implant for providing simultaneous magnetic resonance imaging (MRI) and computed tomographic (CT) imaging contrast is provided. The composite implant may include scaffold and/or beads. The scaffold comprises a calcium compound in the form of nano or microparticle comprising a first dopant and a second dopant. The first dopant is configured to provide MR contrast and the second dopant is configured to provide CT contrast. The scaffold further comprises a biopolymer matrix comprising a polymer. The polymer may comprise one or more of alginate, gelatin, collagen, chitosan, carboxymethyl chitosan, chitin, cellulose, carboxymethyl cellulose, dextran, fibrin, hyaluronic acid, chondroitin sulphate, agarose, starch, poly [lactic-co-glycolic] acid, poly-L-lactic acid, polylactic acid, polycaprolactone, polyvinyl alcohol, polyhydroxy butyrate, polyhydroxy butyrate co hydroxyvalerate, polyphosphazenes, polyurathane, or polyanhydrides, wherein the scaffold comprises 3-dimensional interconnected porosity.

In various embodiments, the calcium compound is may comprise one or more of hydroxyapatite, calcium phosphate, tri-calcium phosphate, calcium sulphate, calcium phosphosilicate or bioglass.

In one embodiment, the form of the composite implant ranges from beads with size ranging between 10 μm to 10 mm, or a shaped structure implantable into an animal body. In one embodiment, the first dopant or the second dopant is included at a concentration from 0.0001-50 wt %/o of the calcium compound.

In one embodiment, the first dopant comprises iron, manganese, terbium, erbium, dysprosium, holmium, thulium, bismuth, barium, strontium, iodine, zirconium, hafnium or aluminium. In one embodiment, the second dopant is comprises molybdenum, tungsten or tantalum.

In one embodiment, the doped calcium nano or micro particles are loaded onto the composite implant from 1-95% by weight of the composite implant. In one embodiment, the biopolymer further comprises one or more agents configured to be released from the composite implant into human or animal tissue. In one embodiment, the 3-dimensional interconnected porosity is configured to provide sites for proliferation and osteogenic differentiation of mesenchymal stem cells.

Further, the present subject matter provides a method of making composite implant capable of providing imaging contrast for magnetic resonance (MRI) and computed tomography (CT). The method comprises mixing one or more precursors for forming a calcium compound in an aqueous solution, adding a first dopant configured to provide MR contrast at a first concentration and a second dopant configured to provide CT contrast at a second concentration, precipitating particles of the calcium compound doped with the first dopant and the second dopant from solution. The first dopant and the second dopant together form 0.0001-50 wt % of the calcium compound. The precipitate particles then washed to remove impurities. To form the composite implant, a suspension of the redispersed particles is mixed with a biopolymer to form a gel. The gel is then lyophilized to form a porous body. The porous body is further cross-linked to form the composite implant. In one embodiment, the method further comprises an additional lyophilizing step after cross-linking.

In one embodiment, the method further comprises adding one or more therapeutic agents to the biopolymer prior to gel formation wherein the one or more agents are configured to be released from the composite implant into human or animal tissue. In one embodiment, the one or more agents include a drug, a growth factor or a bioactive molecule.

In one embodiment, a method of treating a human or animal patient for bone/cartilage injury or defect, comprising implanting the composite implant. In one embodiment, the method further comprises monitoring the progress of treatment using MR imaging, CT imaging or both.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 3A is an SEM picture showing 150-200 micro meter porosity of the scaffold.

FIG. 3B shows cell attachment to surface of the scaffold.

FIG. 3C shows nuclear staining using DAPi demonstrating significant spreading of hMSCs on the scaffold.

FIG. 3D live/dead staining proving the biocompatibility of the scaffold.

DETAILED DESCRIPTION

Figure 1:
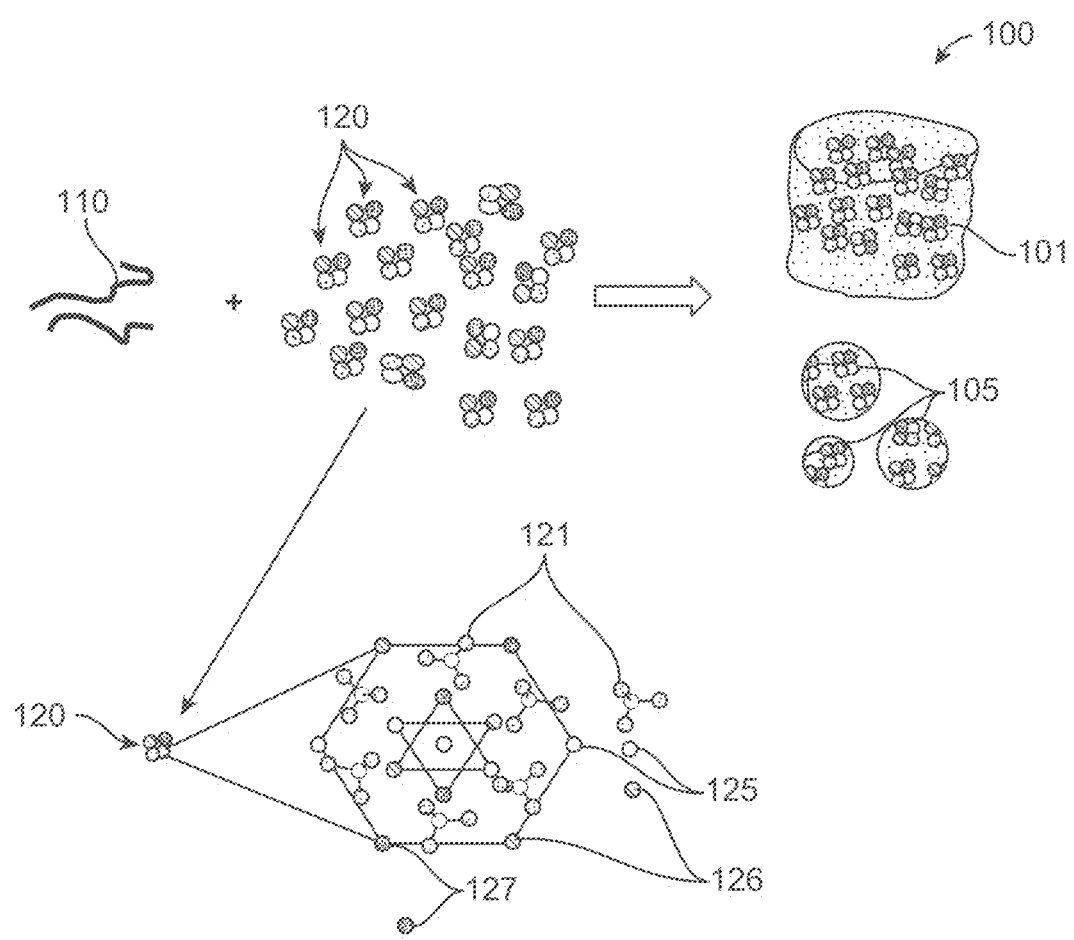
FIG. 1 is a schematic representation of the composite implant.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The present subject matter relates to a composite implant for tissue regeneration, and in particular, to a magnetic resonance imaging (MRI) and computed tomography (CT) contrast enabled osteoconductive scaffold and beads with 3-D interconnected porosity, a method for making the same and a method of using the same in treatment. The composite implant is primarily formed of a calcium compound, a first dopant and a second dopant, and a biopolymer matrix. The composite implant is made by mixing one or more precursors to form a calcium compound in an aqueous solution. The first dopant is configured to provide MRI contrast and the second dopant configured to provide CT contrast.

A schematic representation of the composite implant is illustrated in FIG. 1, according to embodiments of the present subject matter. The composite implant 100 may be in the form of a scaffold 101 or beads 105, and should be understood to refer to either or both of scaffold 101 and beads 105. The scaffold 101 or beads 105 are primarily formed of a calcium compound 120 and a biopolymer matrix 110. In various embodiments, the calcium compound 120 comprises one or more of hydroxyapatite, calcium phosphate, tri-calcium phosphate, calcium sulphate, calcium phosphosilicate or bioglass.

The calcium compounds 120 may be made by mixing a first dopant 126, at a first concentration, and a second dopant 127, at a second concentration. The first dopant 126 may be configured to provide MRI contrast and the second dopant 127 may be configured to provide CT contrast.

In various embodiments, the first dopant 126 may comprise iron, manganese, terbium, erbium, dysprosium, holmium, thulium, bismuth, barium, strontium, iodine, zirconium, hafnium or aluminium. In various embodiments, the second dopant 127 may comprise molybdenum, tungsten or tantalum.

After doping, particles of the calcium compound 120 are loaded onto a biopolymer matrix 110 to form the composite implant. The composite implant may in the form of a gel, a liquid such as emulsions and microemulsions, solution, suspensions, syrups and elixirs or any other suitable dosage forms. The biopolymer matrix 110 may be selected from one or more of alginate, gelatin, collagen, chitosan, carboxymethyl chitosan, chitin, cellulose, carboxymethyl cellulose, dextran, fibrin, hyaluronic acid, chondroitin sulphate, agarose, starch, poly[lactic-co-glycolic] acid, poly-L-lactic acid, polylactic acid, polycaprolactone, polyvinyl alcohol, polyhydroxy butyrate, polyhydroxybutyrate co-hydroxyvalerate, polyphosphazenes, polyurethane, or polyanhydrides. In one embodiment, the biopolymer matrix 110 further comprises one or more agents configured to be released from the scaffold 101 or beads 105 into human or animal tissue.

The scaffold 101 or beads 105 in various embodiments comprise 3-dimensional interconnected porosity 102. In one embodiment, the doped calcium nano or micro particles are loaded onto the scaffold from 1-95% by weight of the scaffold 101. In various embodiments, the form of the ranges from scaffold 101 or beads 105 with size ranging between 10 μm to 10 mm, implantable into a human or animal body.

Figure 2:
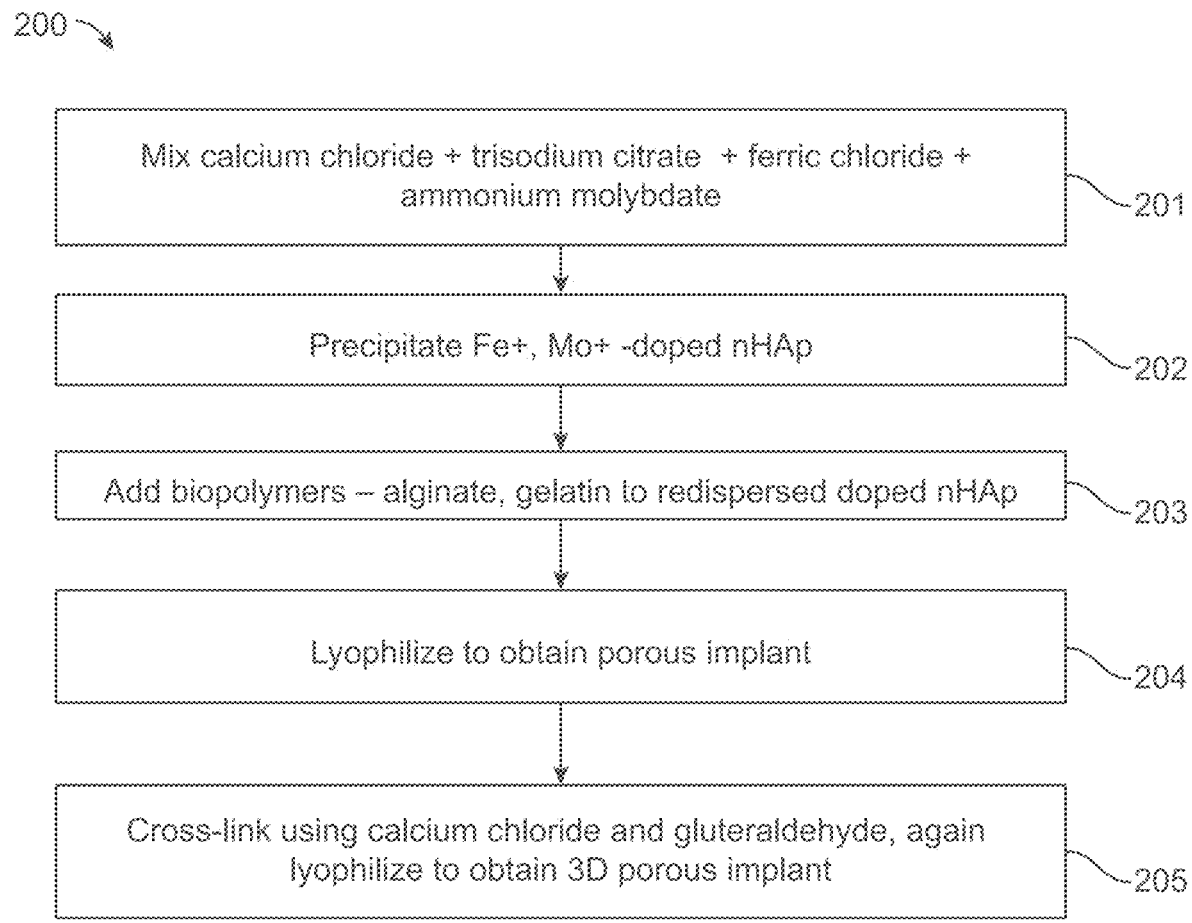
FIG. 2 illustrates the method of producing 3D-porous scaffolds and beads according to embodiments of the invention.

The 3D-porous scaffolds and beads can by produced by a method according to embodiments of the present subject matter, as illustrated in FIG. 2. At step 201, one or more precursors and dopants are mixed for forming the calcium compound in an aqueous solution. In one embodiment, the precursors may include calcium chloride and tri-sodium citrate. The first dopant 126 is added at first concentration and the second dopant 127 at second concentration may be added to the solution.

The doped calcium compound particles are precipitated from the solution, at step 202, such that the first dopant 126 and the second dopant 127 form 0.0001-50 wt % of the calcium compound. For instance, Fe ions, Mo ions, and doped nHAp particles may be separated as precipitate particles from the solution. Further, the precipitate particles may be subjected to washing to remove impurities.

The doped particles are mixed with the biopolymer matrix 110 to form a gel, at step 203. In one embodiment, one or more therapeutic agents may be added to the biopolymer 110 prior to gel formation. The one or more agents may be configured to be released from the scaffold 101 or beads 105 into human or animal tissue. In one embodiment, the one or more agents comprise a drug, a growth factor, or a bioactive molecule.

The gel may be lyophilized to form a porous body of polymer mass, at step 204. After lyophilizing, the polymer is crosslinked to form the composite implant 100, at step 205. In one embodiment, the method further comprises an additional lyophilizing step after cross-linking.

In accordance with further embodiments of the present subject matter, the beads 105 may be prepared by mixing the first dopant 126 and the second dopant 127 with alginate solution. For example, Fe-nHAp/alginate bead 105 may be prepared by mixing specific amounts of Fe-nHAp to alginate solution. The mixture may be blended and added drop wise to calcium chloride solution to form Fe-nHAp/alginate beads 105. The beads 105 may then be strained, washed and dried. Similarly, Mo-nHAp/alginate bead 105 may be prepared by mixing molybdenum doped calcium phosphate nanoparticles in alginate solution. The mixture may be added to calcium chloride to produce the beads or microbeads 105. The beads 105 may then be strained, washed and dried for use in implantation.

The composite implant 100 includes the 3-dimensionally interconnected porosity configured to provide tissue integration and proliferation sites. The tissue integration and proliferation enables treatment of human or animal patient for bone/cartilage injury or defect by implantation. In one embodiment, the 3-D interconnected porosity is configured to provide sites for proliferation and osteogenic differentiation of mesenchymal stem cells. In addition, the chemical composition of the composite implant 100 provides simultaneous imaging contrast with MRI and CT monitoring. Further, the composite implant 100 is structured to enable treatment of human or animal patient for bone/cartilage injury or defect by implantation, with MR and CT monitoring In one embodiment, a method of treating a human or animal patient for bone/cartilage injury or defect, comprising implanting the composite implant 100. In one embodiment, the method further comprises monitoring the progress of treatment using MRI, CT imaging or both.

The invention is further explained in the following examples, which however, are not to be construed to limit the scope of the invention as defined by the appended claims.

EXAMPLES

Example 1: Preparation of Contrast Enhanced 3-D Scaffold 101

Three dimensional porous scaffold 101 was developed by incorporating doped nano-microparticles of calcium compounds into matrix of Alginate (Alg) and Gelatin (Gel) using lyophilization technique. Doped HAp (hydroxyapatite) was synthesized using a previously reported wet chemistry method.

For the synthesis of iron-doped nano HAp, 0.5M calcium chloride ($CaCl_2$, Sigma, USA) was mixed with 20 mL of 0.2M trisodium citrate ($Na_3C_6H_5O_7$, Fisher Scientific, India) and 0.1M $FeCl_3$ (Sigma, USA). Volume of 0.1 M $FeCl_3$ added was varied as per the required percentage of doping. 5 mL of 0.3 M diammonium hydrogen phosphate (($NH_4)_2HPO_4$, S.D Fine Chemicals, India) mixed with 0.2 mL of 3 N ammonium hydroxide ($NH_4OH$, Fisher Scientific, India) was added drop wise to the above mixture of $CaCl_2$, $Na_3C_6H_5O_7$ and $FeCl_3$ under constant stirring to obtain Fe doped calcium phosphate nanoparticles. The precipitate was washed 4 times in hot distilled water by centrifugation at 8500 rpm for 15 minutes and redispersed in PBS.

For the synthesis of molybdenum doped nano HAP, 15 ml of 0.5M calcium chloride ($CaCl_2$, Sigma, USA) was mixed with 0.1M ammonium molybdate (($NH_4)_6Mo_7O_{24}.4H_2O$, Nice chemicals, India). Volume of ammonium molybdate was varied according to the required percentage of doping. 5 ml of 0.3M diammonium hydrogen phosphate (($NH_4)_2HPO_4$, S.D Fine Chemicals, India) was mixed with 3N ammonium hydroxide ($NH_4OH$, Fisher Scientific, India) and added drop-wise to the reaction mixture, under constant stirring. Precipitate washed 5 times with distilled water and centrifugation at 7000 rpm for 10 minutes.

Synthesized doped HAp was mixed with polymeric solution of Alginate and Gelatin and lyophilized. Scaffold was crosslinked using 2% $CaCl_2$ and 0.2% glutaraldehyde and further lyophilized to obtain porous 3-D scaffold.

Example 2: Preparation of Contrast Enhanced Composite Beads 105

For preparing Fe-nHAp/alginate bead, 10 mL of 3 wt % alginate solution was prepared and kept for stirring for 20 minutes until the alginate is completely solubilized. 60 wt % of Fe-nHAp was added to the alginate solution and blended using mortar and pestle or a blender (IKA, US). The blended alginate-Fe-nHAp was added drop wise to 1 wt % calcium chloride solution to form Fe-nHAp/alginate beads 105. The beads were strained, washed thrice with distilled water and dried in hot air oven at 60° C. overnight. For preparation of Mo-nHAp/alginate bead, 1% sodium alginate (Sigma, USA) solution was prepared and under constant stirring the molybdenum doped calcium phosphate nanoparticles (80% w/w of sodium alginate) was added slowly and kept for stirring at room temperature for 2 hours. Using a micro pipette, this alginate-nanoparticle mixture was dropped into 2% (w/v) calcium chloride (Fisher scientific, India) solution to produce the microbeads. The beads were removed after 2 hours form the $CaCl_2$ solution, washed 5 times with distilled water and dried for 24 hours in a hot-air oven (60° C.).

Example 3: Characterization of 3-D Scaffold/Bead

Porous morphology of the developed scaffold is evident from SEM image in FIG. 3A. Pore size of the scaffold ranging from 150-200 μm, as shown in FIG. 3A, facilitates cell growth and proliferation. FIGS. 3B and 3C represent SEM images of mesenchymal stem cells (MSCs) attachment and cell spreading using nuclear staining with DAPI on the scaffold respectively. FIG. 3D represents live/dead imaging of MSCs proving the biocompatibility of the scaffold.

Figure 4A:
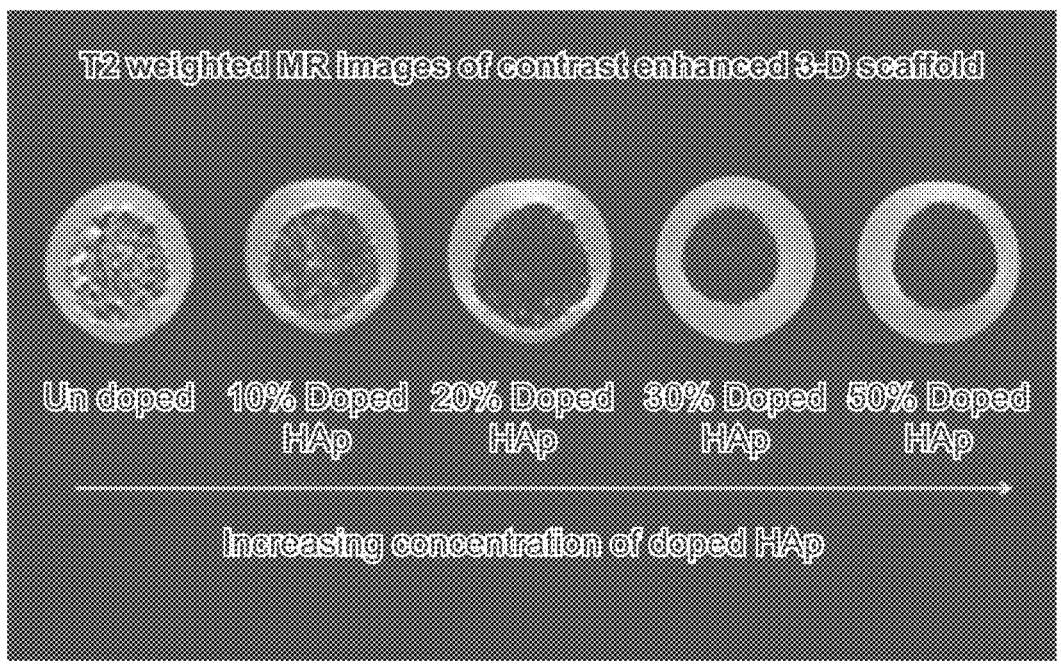
FIG. 4A illustrates T2 weighted MR images of 3-D scaffolds with varying concentrations of MF-nHAp, showing contrast variation with doped HAp content.
Figure 4B:
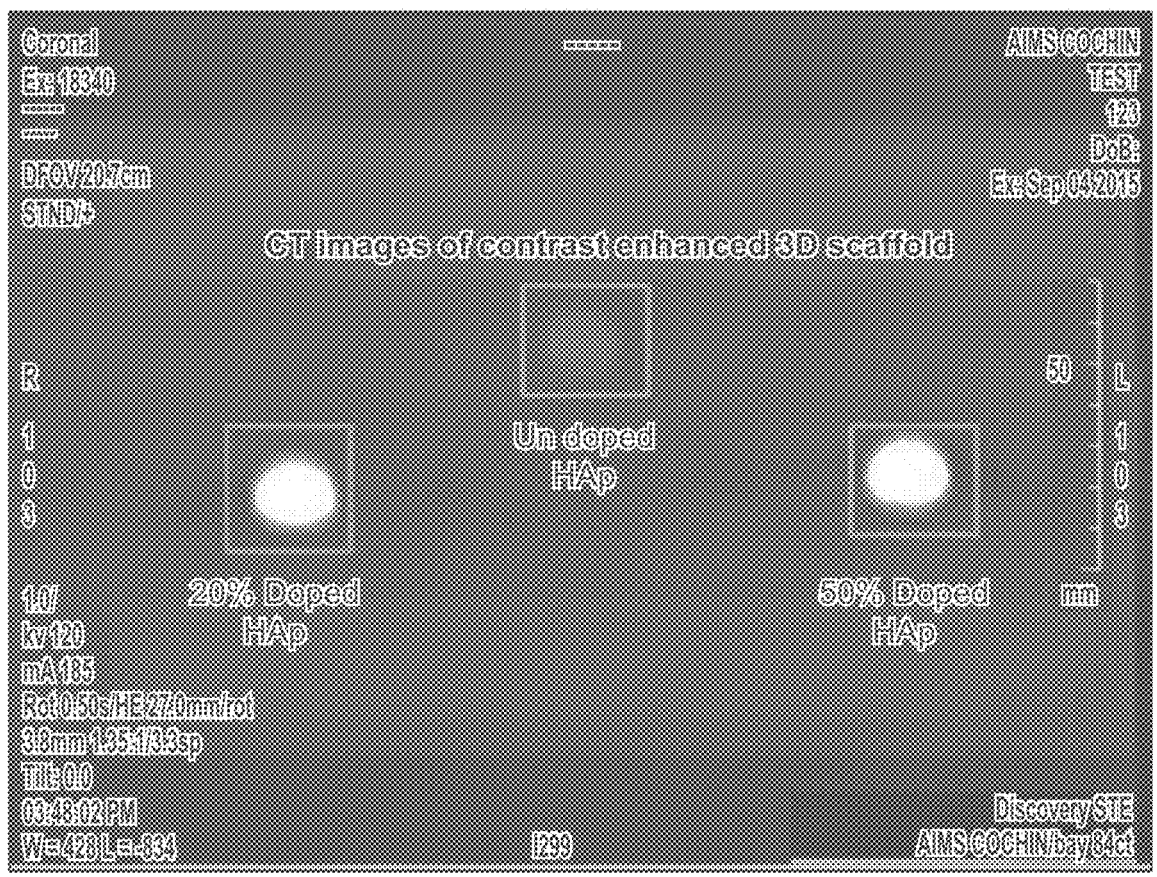
FIG. 4B shows CT images of 3-D scaffold with doped MF-nHAp exhibiting significant contrast compared to scaffold with undoped HAp.

Nano- or micro-doped HAp incorporated scaffold provides an enhanced T2 contrast compared to undoped scaffold due to the T2 shortening by $Fe^{3+}$ ions. FIG. 4A shows the change in MRI contrast with increasing concentration of doped nano-micro HAp from 0-50% and FIG. 4B represents CT images of 3-D scaffold showing change in contrast with respect to incorporation of nano- or micro-particle doped HAp.

Figure 5C:
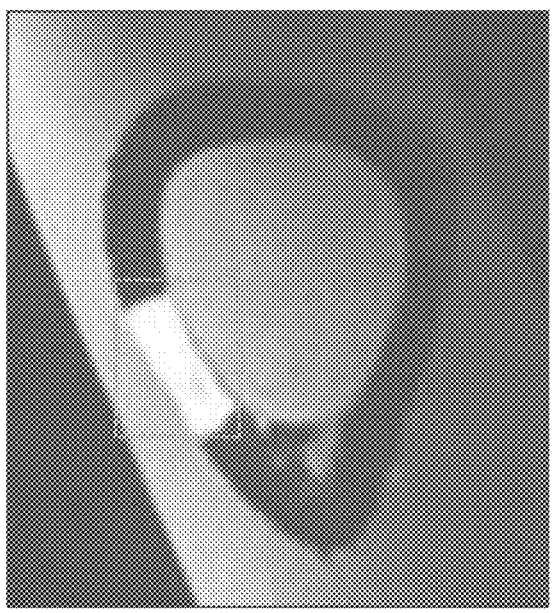
FIG. 5C shows axial T1 weighted MRI with defect region in yellow boxes.
Figures 5A, 5B, 5D:
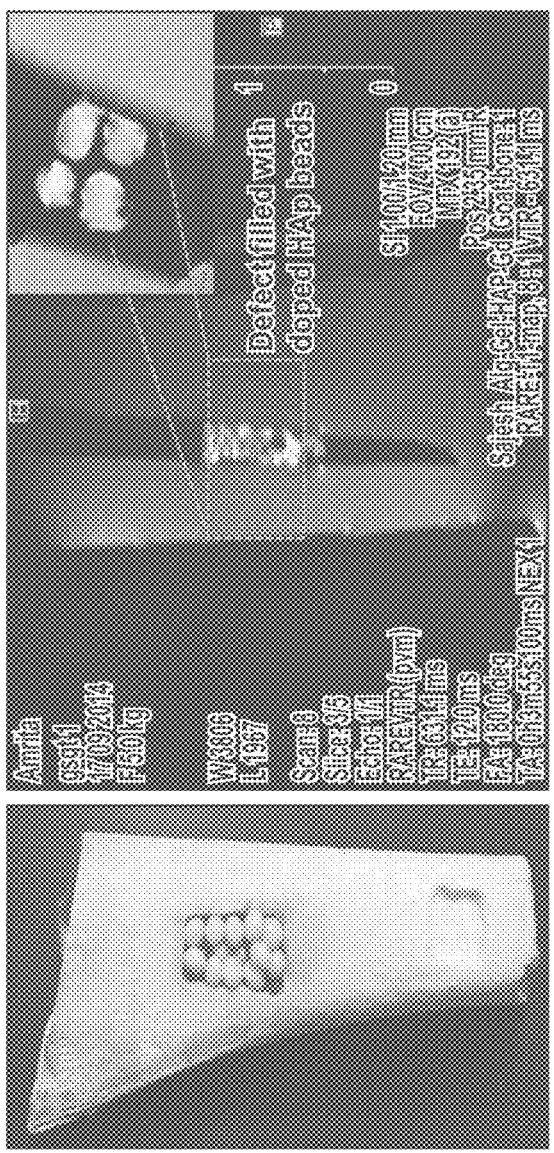
FIG. 5A is a photograph of phantom bone sample filled with doped beads.
FIG. 5B is a sagittal section of T1 weighted MRI of the phantom bone defect filled with MF Hap beads, inset is enlarged image of the bead-filled portion.
FIG. 5D illustrates CT contrast from the MF-Hap beads in different views.

FIG. 5A shows photograph of phantom bone sample filled with doped beads 105. FIG. 5B is a sagittal section of T1 weighted MRI of the phantom bone defect filled with MF (Mo-doped, Fe-doped) HAp beads. Inset shows enlarged image of the bead-filled portion. FIG. 5C is axial T1 weighted MRI of the bone with defect region shown in yellow boxes. Bright T1 weighted contrast is visible from MF beads. FIG. 5D shows CT contrast from the MF-HAp beads.

Figure 6A:
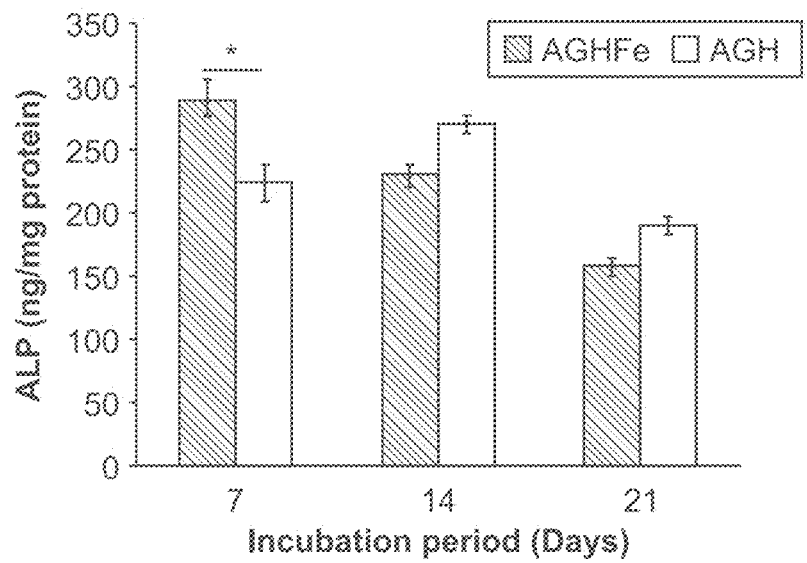
FIG. 6A shows ALP concentration on the scaffold with implantation time.
Figure 6B:
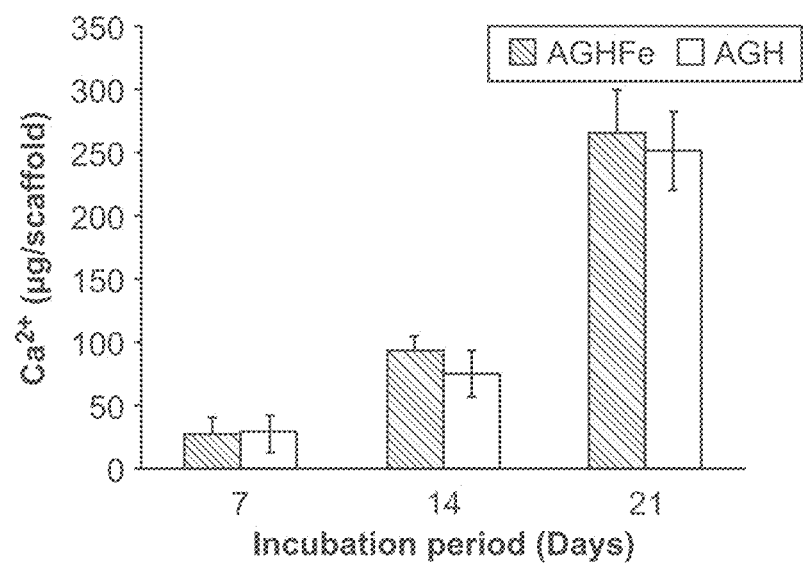
FIG. 6B shows quantification of calcium ion deposition with time.
Figure 6C:
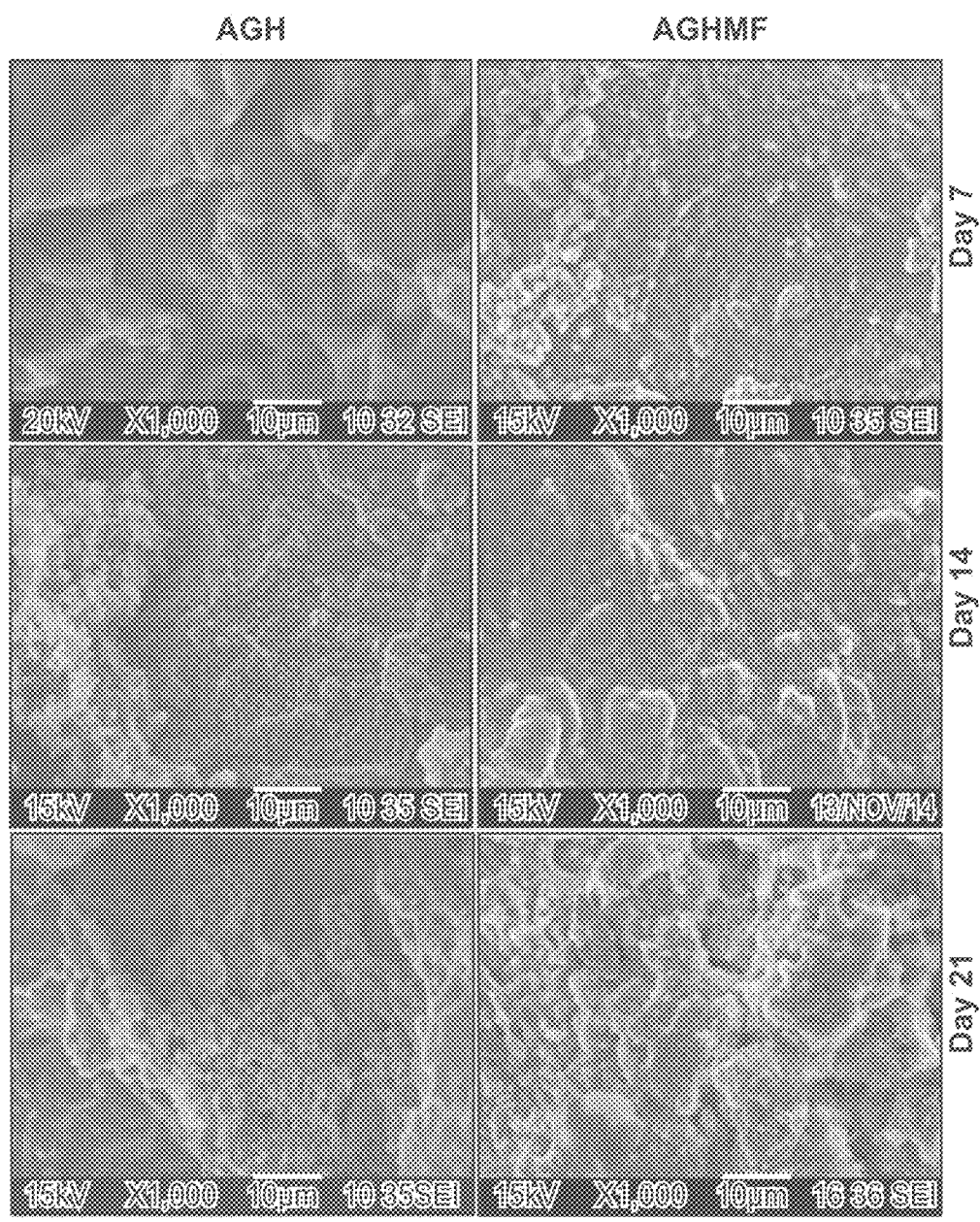
FIG. 6C is an SEM image showing mineral deposition.
Figure 6D:
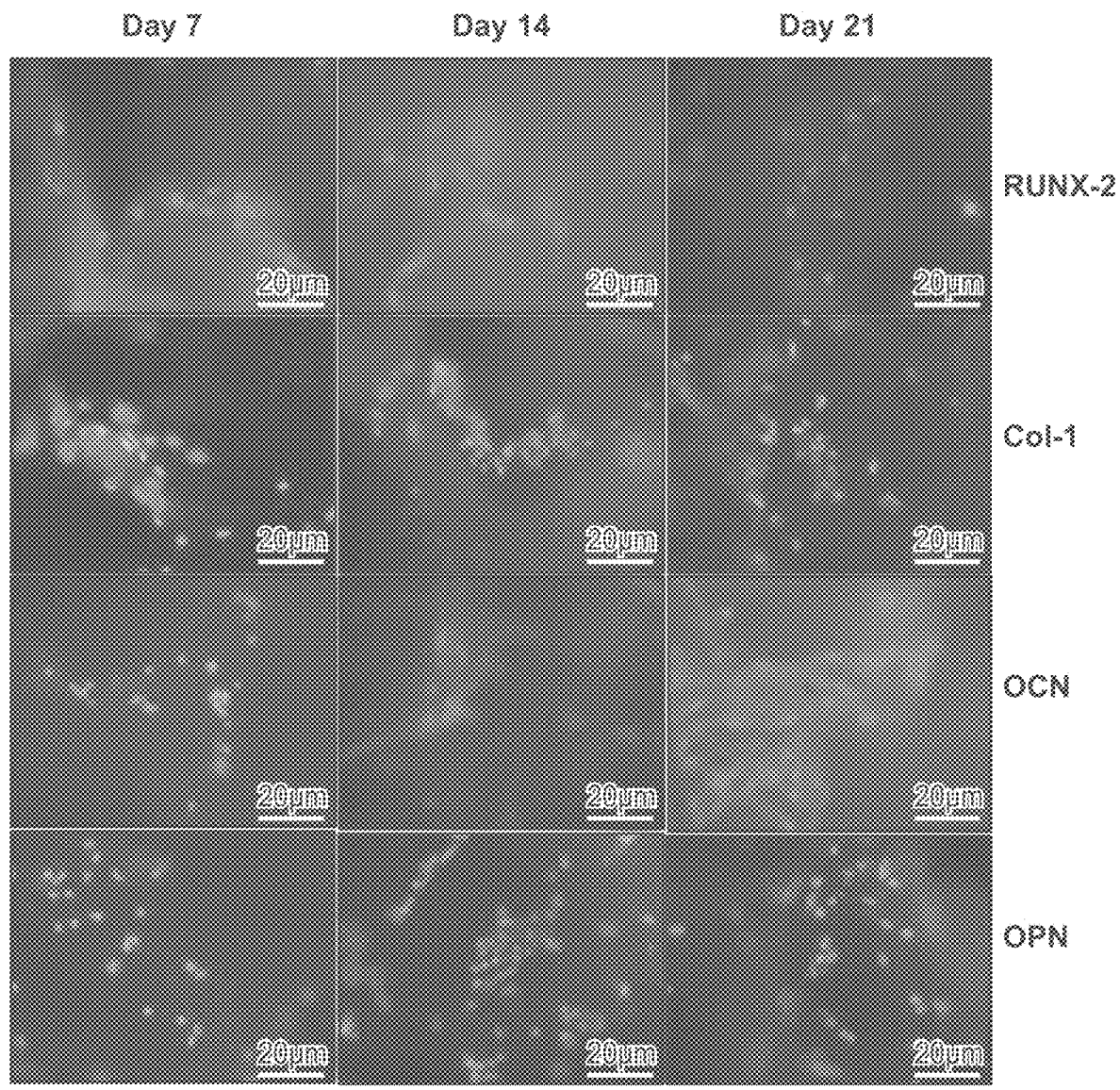
FIG. 6D is a montage of immunoflourescence analysis showing expression of RUNX-2, collagen-1, osteocalcin and osteopontin.

Analysis also proved that, osteogenic potential was not affected by incorporating doped HAp into the scaffold. Differentiation of hMSCs to osteoblast on the developed scaffolds was analyzed by measuring the ALP concentration, which is an early marker of osteogenesis. A considerable enhancement in ALP was observed (FIG. 6A), which may be attributed by the osteoconducting property of HAp. Maturation of osteoblasts was confirmed by analyzing mineral deposition (FIG. 6B) on the scaffold and further proved by quantifying the deposited calcium ions (FIG. 6C). Immunofluorescent analysis (FIG. 6D) shows expression of osteogenic specific proteins like RUNX-2, collagen-1, osteocalcin and osteopontin.

Figure 7A:
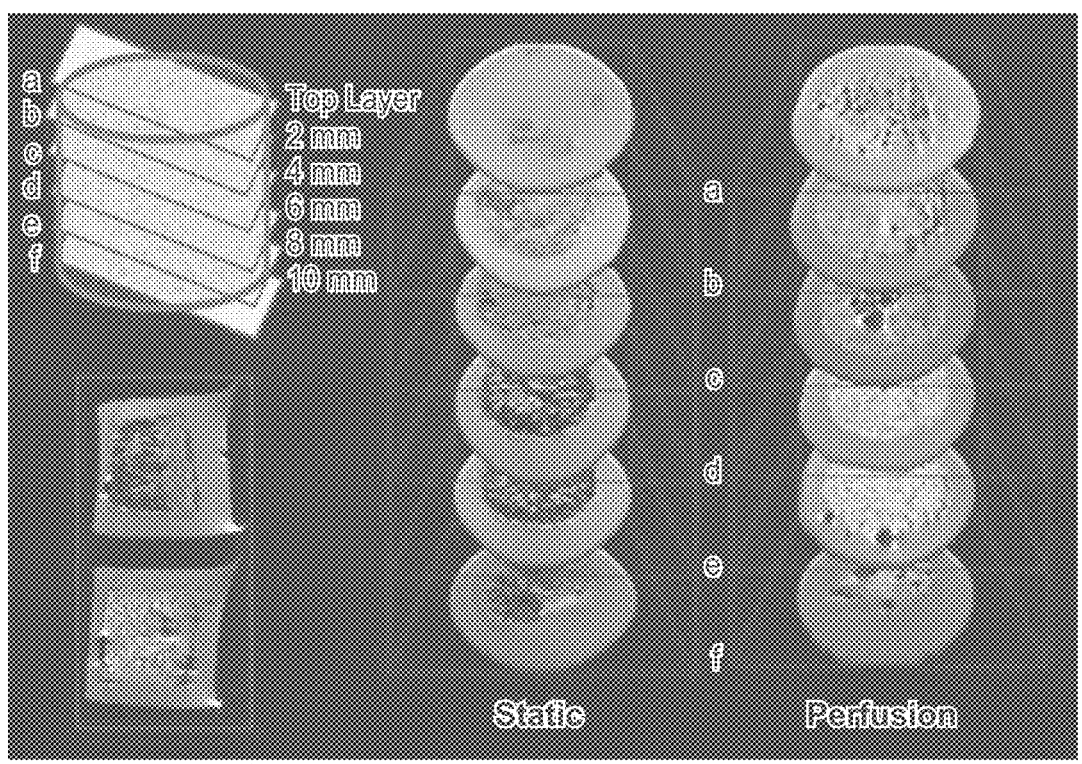
FIG. 7A shows stacked MR images illustrating uniform cell distribution throughout the 3-D scaffold in perfusion culture when compared to static culture.
Figure 7B:
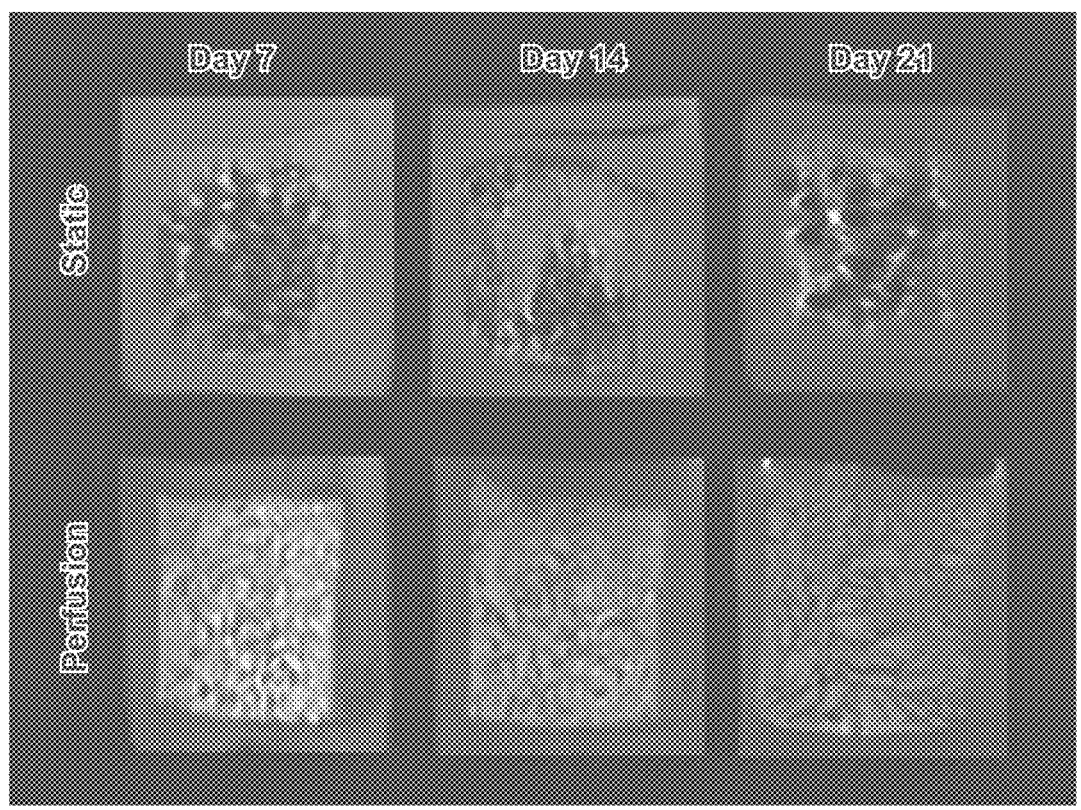
FIG. 7B shows T2 weighted MRI of 3D scaffold showing matrix deposition at day 7, 14 and 21.

FIGS. 7A and 7B represent the MR images of doped 3-D scaffold cultured in a perfusion bioreactor for analyzing ex-vivo tissue growth. In FIG. 7A, the white spots seen in the scaffold are cells growing into the scaffold and the MR image demonstrates cell infiltration throughout the 3-D scaffold when cultured in perfusion system. FIG. 7B shows distinct changes in the MR contrast with regard to matrix deposition and morphological change when cultured ex vivo for 21 days.

Figure 8A:
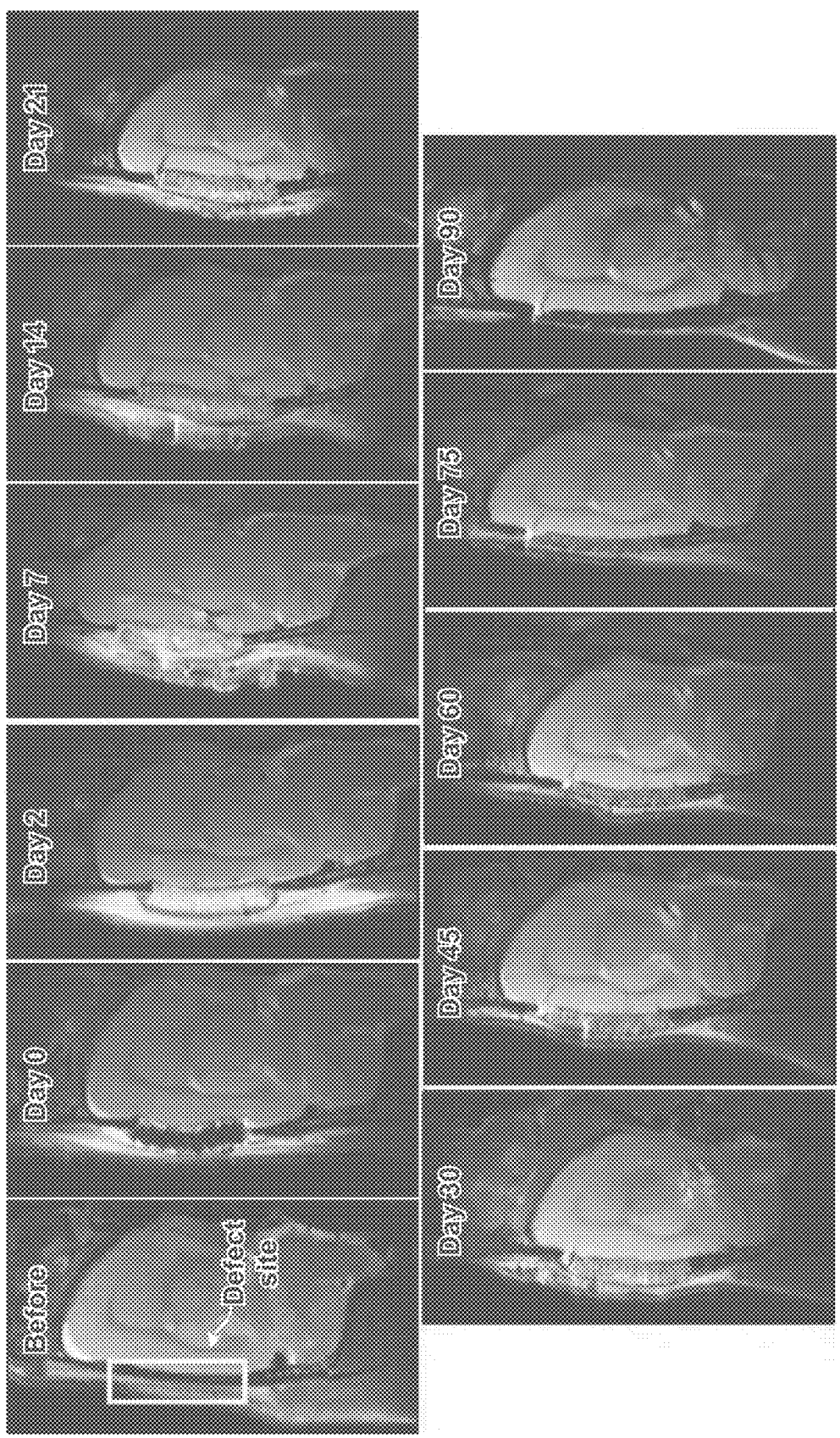
FIG. 8A shows in vivo T2 weighted MR images of AGHMF scaffold implanted in rat cranial defect, up to 3 months after implantation.
Figure 8B:
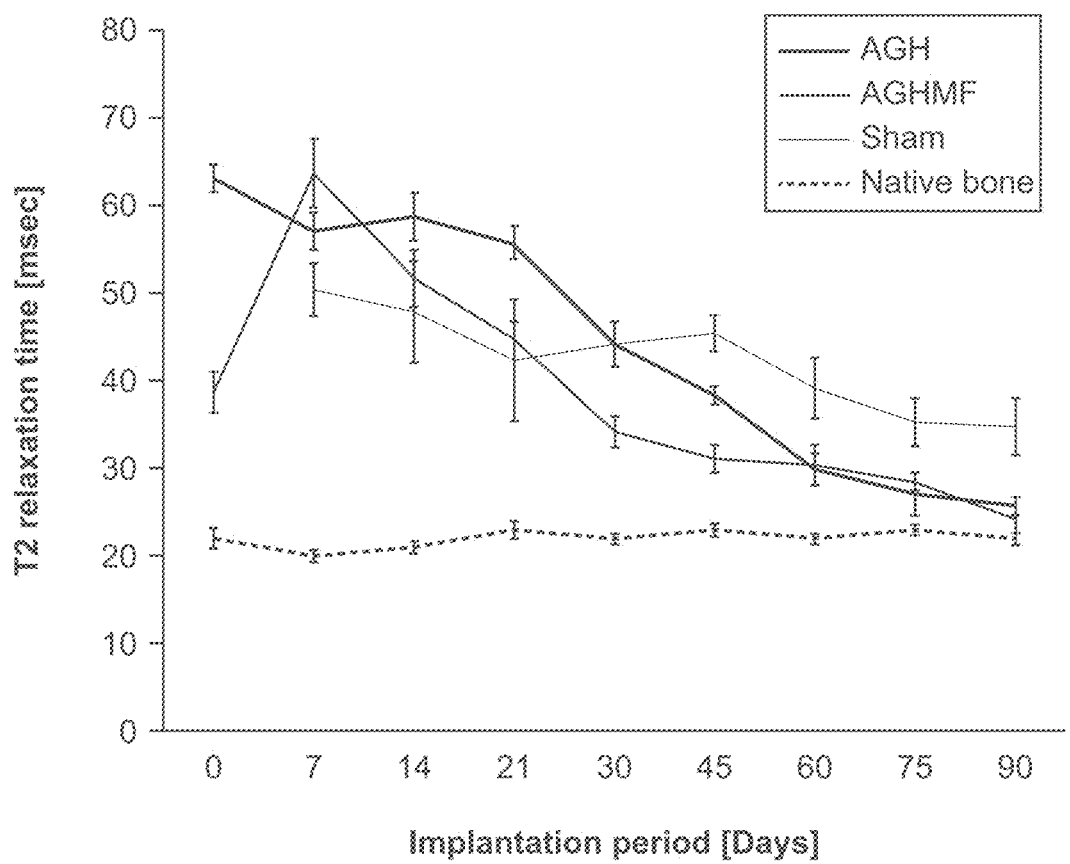
FIG. 8B illustrates T2 relaxation time mapping of implanted scaffolds from day 0 to 90.

FIG. 8A represents MR images of doped nano- or micro-HAp incorporated 3-D scaffold implanted in rat cranial defect and non-invasive analysis of bone regeneration up to a time period of 90 days. Implanted scaffold was located using MRI with dark contrast and cell infiltration into the scaffold was characterized with bright contrast. MR images could also demonstrate the swelling, which could be due to the immune response to the implant. Continuous monitoring up to 90 days shows change in contrast change with respect to matrix deposition and tissue maturation. FIG. 8B represents change in T2 relaxation values post implantation with respect to tissue regeneration. Significant change in T2 values were observed with regard to cellular activity and physiological alterations during the regenerative processes.

Figure 9A:
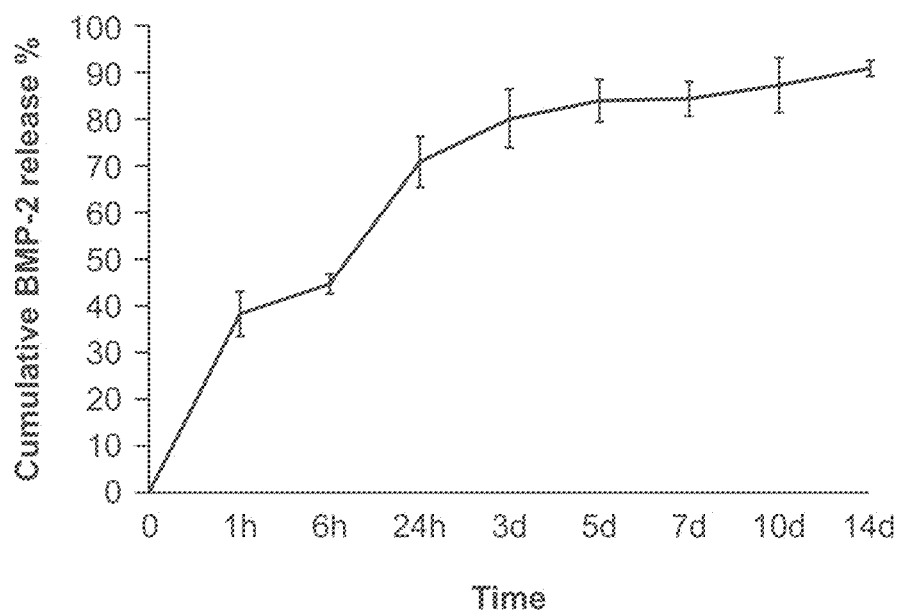
FIG. 9A shows release profile of BMP-2 growth factor from the scaffold.
Figure 9B:
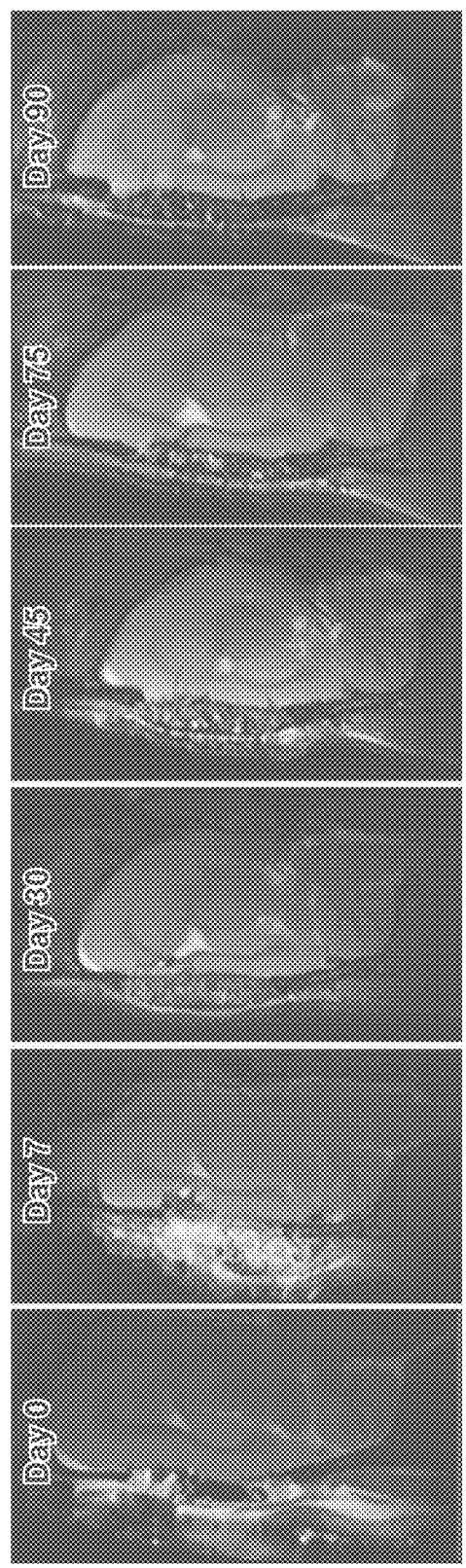
FIG. 9B includes T2 weighted MR images of BMP-2 loaded AGHMF scaffold implanted in rat cranial defect.

Histological analysis of the AGHMF (Mo-doped, Fe-doped HaP nanoparticles with alginate-gelatin matrix) scaffold was done 3 months post implantation. Vascularization in the implantation site and trichrome staining illustrated deposition of collagen fibers. Immunohistochemical staining of osteocalcin throughout the defect further revealed the osteogenic potential of developed MR contrast scaffold. The developed scaffold can be utilized for sustained delivery of drugs/growth factors. BMP-2 is a well-known osteoinductive agent and is being utilized for enhanced bone formation and to aid bone defect healing. Accounting on the preferential binding with HAp, BMP-2 was loaded into the 3-D scaffold for controlled delivery. Release profile study using ELISA (FIG. 9A) shows an initial burst release and sustained delivery of BMP-2 growth factor from the scaffold in low doses up to a time period of 14 days. When implanted in rat cranial defect, contrast property of the scaffold facilitated non-invasive monitoring of influence of BMP-2 in in vivo bone regeneration using MRI (FIG. 9B).

While the above is a complete description of the embodiments of the invention, various alternatives, modifications, and equivalents may be used. Therefore, the above description and the examples should not be taken as limiting the scope of the invention which is defined by the appended claims.

What is claimed is:

1. A composite implant comprising a scaffold or beads for providing simultaneous magnetic resonance imaging (MRI) and computed tomographic (CT) imaging contrast, comprising:
   a calcium compound in the form of nano- or micro-particle comprising a first dopant selected from bismuth, strontium, iodine, zirconium, hafnium or aluminum and a second dopant, wherein the first dopant is configured to provide MRI contrast and the second dopant is configured to provide CT contrast; and
   a biopolymer matrix comprising a polymer, wherein the polymer comprises alginate, gelatin, collagen, chitosan, carboxymethyl chitosan, chitin, cellulose, carboxymethyl cellulose, dextran, fibrin, hyaluronic acid, chondroitin sulphate, agarose, starch, poly[lactic-co-glycolic] acid, poly-L-lactic acid, polylactic acid, polycaprolactone, polyvinyl alcohol, polyhydroxy butyrate, polyhydroxy butyrate co hydroxyvalerate, polyphosphazenes, polyurathane, or polyanhydrides;
   wherein the scaffold or beads comprise 3-dimensional interconnected porosity of size 150-200 µm.

2. The composite implant of claim 1, wherein the calcium compound comprises hydroxyapatite, calcium phosphate, tri-calcium phosphate, calcium sulphate, calcium phosphosilicate or bioglass.

3. The composite implant of claim 1, wherein the form of the composite implant comprises scaffolds or beads with size ranging between 10 µm to 10 mm, or a shaped structure implantable into an animal body.

4. The composite implant of claim 1, wherein the first dopant or the second dopant is included at a concentration from 0.0001- 50 wt % of the calcium compound.

5. The composite implant of claim 1, wherein the second dopant comprises molybdenum, tungsten or tantalum.

6. The composite implant of claim 1, wherein the doped calcium nano or micro particles are loaded onto the scaffold from 1-95% by weight of the scaffold.

7. The composite implant of claim 1, wherein the biopolymer further comprises one or more agents configured to be released from the scaffold into human or animal tissue.

8. The composite implant of claim 1, wherein the 3-dimensional interconnected porosity is configured to provide sites for proliferation and osteogenic differentiation of mesenchymal stem cells.

9. A method of making a composite implantable scaffold or beads capable of providing imaging contrast for magnetic resonance (MM) and computed tomography (CT), comprising:
   mixing one or more precursors for forming a calcium compound in an aqueous solution;
   adding a first dopant selected from bismuth, strontium, iodine, zirconium, hafnium or aluminum configured to provide MRI contrast at a first concentration and a second dopant configured to provide CT contrast at a second concentration;

precipitating particles of the calcium compound doped with the first dopant and the second dopant from solution, wherein the first dopant and the second dopant together form 0.0001- 50 wt % of the calcium compound;

washing the precipitate particles to remove impurities;

mixing a suspension of the redispersed particles with a biopolymer to form a gel;

lyophilizing the gel to form a porous body; and crosslinking the polymer to form the scaffold or beads;

wherein the scaffold or beads comprise 3-dimensional interconnected porosity of size 150-200 μm.

10. The method of claim 9, further comprising adding one or more therapeutic agents to the biopolymer prior to gel formation wherein the one or more agents are configured to be released from the composite implant into human or animal tissue.

11. The method of claim 9, wherein the one or more agents comprises a drug, a growth factor or a bioactive molecule.

12. The method of claim 9, further comprising an additional lyophilizing step after cross-linking.

13. A method of treating a human or animal patient for bone/cartilage injury or defect, comprising implanting the composite implant of claim 1.

14. The method of claim 13, further comprising monitoring the progress of treatment using MRI, CT imaging or both.

* * * * *